US00PP14732P2

(12) United States Plant Patent
Brown

(10) Patent No.: US PP14,732 P2
(45) Date of Patent: Apr. 27, 2004

(54) ARCTOTIS PLANT NAMED 'ARCHNAH'

(50) Latin Name: *Arctotis×hybrida*
Varietal Denomination: Archnah

(75) Inventor: Graham Noel Brown, Baulkham Hills (AU)

(73) Assignee: Nuflora International Pty Ltd., New South Wales (AU)

( * ) Notice: Subject to any disclaimer, the term of this patent is extended or adjusted under 35 U.S.C. 154(b) by 0 days.

(21) Appl. No.: 10/385,237

(22) Filed: Mar. 10, 2003

(51) Int. Cl.[7] ..... A01H 5/00
(52) U.S. Cl. ..... Plt./263
(58) Field of Search ..... Plt./263

*Primary Examiner*—Bruce R. Campell
*Assistant Examiner*—A. Para
(74) *Attorney, Agent, or Firm*—C. A. Whealy

(57) ABSTRACT

A distinct cultivar of Arctotis plant named 'Archnah', characterized by its compact, upright and mounded plant habit; freely branching growth habit; and orange red-colored ray florets and nearly black-tipped disc florets with orange-colored pollen.

1 Drawing Sheet

Botanical classification/cultivar designation: *Arctotis×hybrida* cultivar Archnah.

BACKGROUND OF THE INVENTION

The present Invention relates to a new and distinct cultivar of Arctotis plant, botanically known as *Arctotis×hybrida,* and hereinafter referred to by the name 'Archnah'.

The new Arctotis is a product of a planned breeding program conducted by the Inventor in Cobbitty, New South Wales, Australia. The objective of the breeding program is to create new compact Arctotis cultivars that flower early and have interesting floret colors.

The new Arctotis originated from a cross made by the Inventor in 1998 of the *Arctotis×hybrida* cultivar Flame, not patented, as the female, or seed, parent with the *Arctotis× hybrida* cultivar Silver Carpet, not patented, as the male, or pollen, parent. The new Arctotis was discovered and selected by the Inventor as a single flowering plant within the progeny of the stated cross grown in a controlled environment in Cobbitty, New South Wales, Australia, in May, 1999.

Asexual reproduction of the new Arctotis by terminal vegetative cuttings was first conducted in Cobbitty, New South Wales, Australia in May, 1999. Asexual reproduction by cuttings has shown that the unique features of this new Arctotis are stable and reproduced true to type in successive generations.

SUMMARY OF THE INVENTION

The cultivar Archnah has not been observed under all possible environmental conditions. The phenotype may vary somewhat with variations in environment such as temperature, daylength and light intensity without, however, any variance in genotype.

The following traits have been repeatedly observed and are determined to be the unique characteristics of 'Archnah'. These characteristics in combination distinguish 'Archnah' as a new and distinct Arctotis:

1. Compact, upright and mounded plant habit.
2. Freely branching growth habit.

3. Orange red-colored ray florets and nearly black-tipped disc florets with orange-colored pollen.

Plants of the new Arctotis are most similar to plants of the female parent, the cultivar Flame. In side-by-side comparisons conducted in Cobbitty, New South Wales, Australia, plants of the new Arctotis differed from plants of the cultivar Flame in the following characteristics:

1. Plants of the new Arctotis were more compact than plants of the cultivar Flame.
2. Flowers of plants of the new Arctotis had orange red-colored ray florets whereas flowers of plants of the cultivar Flame had orange-colored ray florets.

Plants of the new Arctotis can also be compared to plants of the male parent, the cultivar Silver Carpet. In side-by-side comparisons conducted in Cobbitty, New South Wales, Australia, plants of the new Arctotis differed from plants of the cultivar Silver Carpet in the following characteristics:

1. Plants of the new Arctotis were more upright than and not as spreading as plants of the cultivar Silver Carpet.
2. Leaves of plants of the new Arctotis were green in color whereas leaves of plants of the cultivar Silver Carpet were gray in color.
3. Flowers of plants of the new Arctotis had orange red-colored ray florets whereas flowers of plants of the cultivar Silver Carpet had pink-colored ray florets.

Plants of the new Arctotis differ from plants of the cultivar Archley, disclosed in a U.S. Plant Patent application filed concurrently, primarily in plant size, branching habit, leaf color and ray floret color.

BRIEF DESCRIPTION OF THE PHOTOGRAPHS

The accompanying colored photographs illustrate the overall appearance of the new Arctotis showing the colors as true as it is reasonably possible to obtain in colored reproductions of this type. Colors in the photographs may differ from the color values cited in the detailed botanical description which accurately describe the colors of the new Arctotis.

The photograph at the top of the sheet comprises a side perspective view of a typical flowering plant of 'Archnah' grown in a 15-cm container.

The photograph at the bottom of the sheet is a close-up view of typical inflorescences of 'Archnah'.

DETAILED BOTANICAL DESCRIPTION

The aforementioned photographs and following observations and measurements describe plants grown in Bonsall, Calif., in an outdoor nursery during the late spring and early summer under full sun conditions with day temperatures ranging from 18 to 35° C. and night temperatures ranging from 7 to 18° C. After planting rooted cuttings, plants were grown for about six to eight weeks in 15-cm containers. Color references are made to The Royal Horticultural Society Colour Chart, 1995 edition, except where general terms of ordinary dictionary significance are used.

Botanical classification: *Arctotis×hybrida* cultivar Archnah.

Parentage:

*Female, or seed, parent.*—*Arctotis×hybrida* cultivar Flame, not patented.

*Male, or pollen, parent.*—*Arctotis×hybrida* cultivar Silver Carpet, not patented.

Propagation:

*Type.*—Terminal vegetative cuttings.

*Time to initiate rooting.*—About 12 days at 25° C.

*Root description.*—Fine, fibrous and well-branched.

Plant description:

*Appearance.*—Perennial herbaceous container and garden plant. Compact, upright and mounded plant habit. Freely branching, about ten lateral branches develop per plant; tight clumping habit. Moderately vigorous growth habit.

*Plant height, soil level to top of foliage.*—About 16 cm.

*Plant height, soil level to top of inflorescences.*—About 21 cm.

*Plant width or area of spread.*—About 25 cm.

*Lateral branches.*—Length: About 4 to 5 cm. Diameter: About 8 mm. Internode length: About 5 mm. Aspect: Upright. Strength: Strong. Texture: Pubescent. Color: 157B.

*Foliage description.*—Arrangement: Alternate; simple. Number of leaves per lateral branch: About 8 to 10. Length: About 7 cm. Width: About 4 cm. Shape: Roughly elliptic; irregularly lobed. Apex: Broadly acute. Base: Attenuate. Margin: Entire with irregular lobes, about five to seven lobes per leaf. Venation pattern: Pinnate. Texture, upper and lower surfaces: Pubsecent. Color: Young foliage, upper surface: 147D. Young foliage, lower surface: 157A. Fully expanded foliage, upper surface: 147A. Fully expanded foliage, lower surface: 188A. Venation, upper surface: 194A. Venation, lower surface: 146B. Petiole: Length: About 4.5 cm. Diameter: About 4 mm. Texture, upper and lower surfaces: Glabrous. Color, upper surface: 147C. Color, lower surface: 146C.

Inflorescence description:

*Appearance.*—Single axillary inflorescences held above and beyond the foliage on strong peduncles. Composite inflorescence form, radially symmetrical, with ligulate-shaped ray florets and disc florets massed at the center; ray and disc florets develop acropetally on a capitulum. Inflorescences persistent. Inflorescences face upright or outward.

*Flowering response.*—Plants flower continuous and freely from the spring through the fall.

*Postproduction longevity.*—Inflorescences maintain good color and substance for about five to ten days on the plant when grown in an outdoor environment.

*Quantity of inflorescences.*—About 30 open inflorescences and inflorescence buds per plant.

*Fragrance.*—None detected.

*Inflorescence bud (at stage of showing color).*—Length: About 1.8 cm. Diameter: About 1.4 cm. Shape: Roughly spherical. Color, ray florets, lower or outer surface: 31A.

*Inflorescence size.*—Diameter: About 6.2 cm. Depth (height): About 2.2 cm. Disc diameter: About 1.7 cm. Receptacle diameter: About 1.8 cm. Receptacle height: About 1.4 cm.

*Ray florets.*—Length: About 3 cm. Width: About 6 mm. Shape: Ligulate, elliptic. Apex: Broadly acute. Base: Attenuate. Margin: Entire. Texture, upper and lower surfaces: Smooth, satiny. Orientation: Initially upright then about 10 to 15° from perpendicular; recurving. Number of ray florets per inflorescence: About 28 in a single whorl. Color: When opening, upper surface: Darker and brighter than 169A; towards the apex, 25A. When opening, lower surface: 25B. Fully opened, upper surface: Darker and brighter than 169A; towards the apex and towards the base, 24A. Fully opened, lower surface: Ground color, 25B, overlain with fine longitudinal stripes, 171B to 171C.

*Disc florets.*—Shape: Tubular, elongated; fused at base. Apex: Five-pointed. Length: About 7 mm. Width: At apex: About 2 mm. At base: About 1 mm. Number of disc florets per inflorescence: About 168. Color: Immature: Close to 202A. Mature, apex: Close to 202A. Mature, mid-section: 199A to 199B. Mature, base: 157A.

*Phyllaries.*—Length: About 5 mm. Diameter: About 3.5 mm. Shape: Elliptical. Apex: Broadly acute. Base: Fused. Margin: Entire. Texture: Slightly pubescent. Number per inflorescence: About 48 in about three or four whorls. Color: Upper surface: 146A. Lower surface: 146C.

*Peduncles.*—Length: About 13 cm. Diameter: About 4 mm. Angle: Mostly upright. Strength: Strong. Texture: Pubescent. Color: 148D.

*Reproductive organs.*—Androecium: Present on ray and disc florets. Stamen number: Five per floret; fused around style. Anther shape: Elongated oblong. Anther length: About 1.5 mm. Anther color: 23A. Pollen amount: Moderate. Pollen color: 23A. Gynoecium: Present on ray florets only. Pistil number: One per floret. Pistil length: About 7 mm. Stigma shape: Two-parted. Stigma color: 173A. Style length: About 4 mm. Style color: 23B. Ovary color: 157A.

*Seed/fruit.*—Seed and/or fruit production has not been observed.

Disease/pest resistance: Resistance to pathogens and pests common to Arctotis has not been observed on plants grown under commercial greenhouse or outdoor conditions.

It is claimed:

1. A new and distinct cultivar of Arctotis plant named 'Archnah', as illustrated and described.

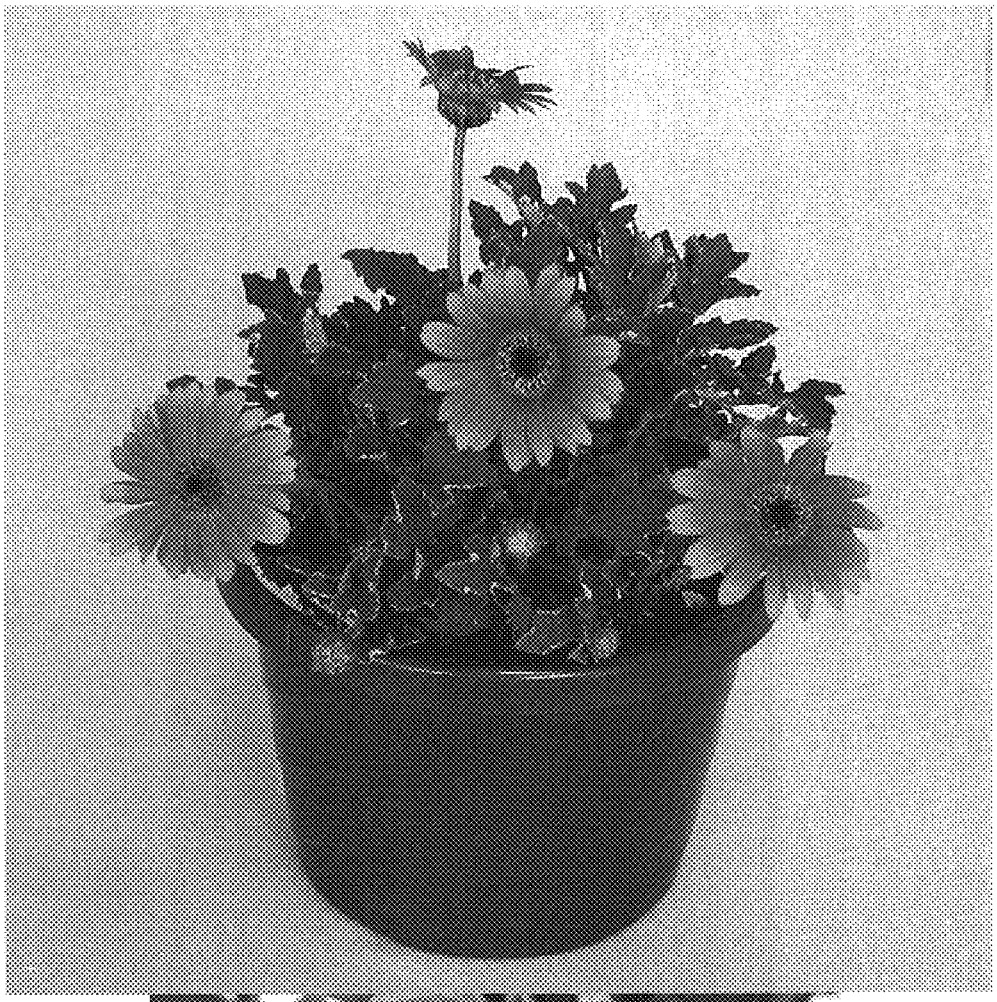
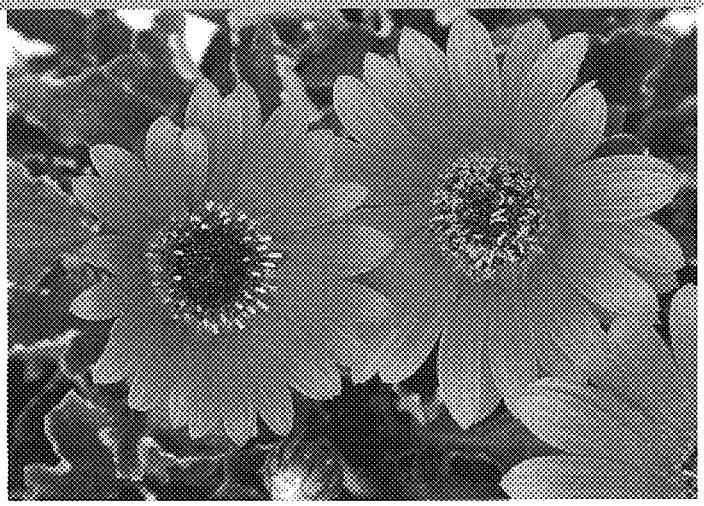

* * * * *